US010234669B2

(12) United States Patent
Fan et al.

(10) Patent No.: US 10,234,669 B2
(45) Date of Patent: Mar. 19, 2019

(54) ZOOM OBJECTIVE LENS OF OPERATING MICROSCOPE

(71) Applicant: ZUMAX MEDICAL CO., LTD, Suzhou, Jiangsu (CN)

(72) Inventors: Bing Fan, Suzhou (CN); Jianyue Li, Suzhou (CN); Xiaofeng Zhou, Suzhou (CN); Jilong Wang, Suzhou (CN); Xiaohu Liu, Suzhou (CN)

(73) Assignee: ZUMAX MEDICAL CO., LTD, Suzhou (CN)

( * ) Notice: Subject to any disclaimer, the term of this patent is extended or adjusted under 35 U.S.C. 154(b) by 287 days.

(21) Appl. No.: 15/305,736

(22) PCT Filed: Dec. 29, 2014

(86) PCT No.: PCT/CN2014/095429
§ 371 (c)(1),
(2) Date: Oct. 21, 2016

(87) PCT Pub. No.: WO2015/161665
PCT Pub. Date: Oct. 29, 2015

(65) Prior Publication Data
US 2017/0052357 A1 Feb. 23, 2017

(30) Foreign Application Priority Data
Apr. 25, 2014 (CN) .......................... 2014 1 0171856

(51) Int. Cl.
*G02B 21/02* (2006.01)
*G02B 7/10* (2006.01)
(Continued)

(52) U.S. Cl.
CPC ............ *G02B 21/025* (2013.01); *A61B 90/20* (2016.02); *G02B 7/10* (2013.01); *G02B 15/161* (2013.01); *G02B 21/0012* (2013.01)

(58) Field of Classification Search
CPC ................ G02B 21/025; G02B 15/161; G02B 21/0012; G02B 7/10
See application file for complete search history.

(56) References Cited

U.S. PATENT DOCUMENTS

2014/0049816 A1* 2/2014 Nauli ................. G02B 21/0012
359/383

FOREIGN PATENT DOCUMENTS

CN 2422656 3/2001
CN 2606364 3/2004
(Continued)

OTHER PUBLICATIONS

International Search Report dated Apr. 3, 2015.

*Primary Examiner* — Joseph P Martinez

(57) ABSTRACT

Disclosed is a zoom objective lens (16) of an operating microscope (10), wherein the zoom objective lens (16) and a lens cone of the operating microscope (10) are provided along a same axis (24). The zoom objective lens (16) comprises a positive lens group (11) and a negative lens group (12) provided along a same axis (24). The positive lens group (11) is provided on an objective lens holder (14), and the negative lens group (12) is provided on a negative lens group holder (15) and directly faces the object under observation (G). The zoom objective lens (16) is changeably connected to a body (20) of the operating microscope through the objective lens holder (14) or a coupling holder, the negative lens group holder (15) is capable of moving in the optical axis (24) direction relative to the objective lens holder (14), and the position of the objective lens holder (14) relative to an illumination system (21) and an observation system (22) remains unchanged. The focus length of this zoom objective lens (16) can be continuously adjusted, and the zoom objective lens can be replaced as a whole. The structures of the illumination system (21) and the observa- (Continued)

tion system (22) of the operating microscope (10) can remain unchanged, and in the zooming process, the positions of the zoom objective lens (16) relative to the illumination system (21) and the observation system (22) remain unchanged. In the zoom objective lens (16), a guide mechanism (17) for leading the negative lens group holder (15) to move in the optical axis (24) direction, and a drive mechanism (18) for driving the negative lens group holder (15) to move in the optical axis (24) direction are provided, thereby causing that the zoom objective lens (16) have a compact structure and is convenient to adjust.

18 Claims, 5 Drawing Sheets

(51) Int. Cl.
  *A61B 90/20* (2016.01)
  *G02B 21/00* (2006.01)
  *G02B 15/16* (2006.01)

(56) References Cited

FOREIGN PATENT DOCUMENTS

| | | |
|---|---:|---:|
| CN | 2791673 | 11/2010 |
| CN | 201637924 | 11/2010 |
| CN | 201654314 | 11/2010 |
| CN | 103592751 | 2/2014 |
| JP | H0876017 | 3/1996 |

\* cited by examiner

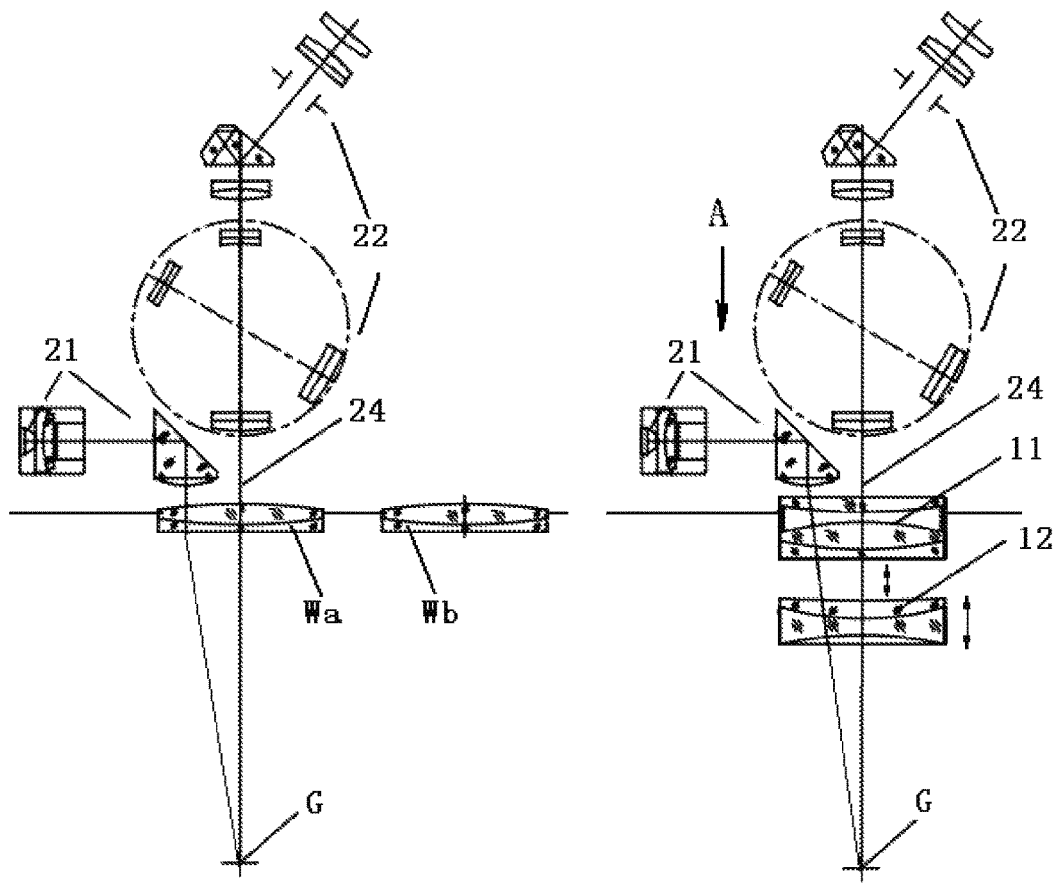
-- Prior Art --
Figure 1a
Figure 1b
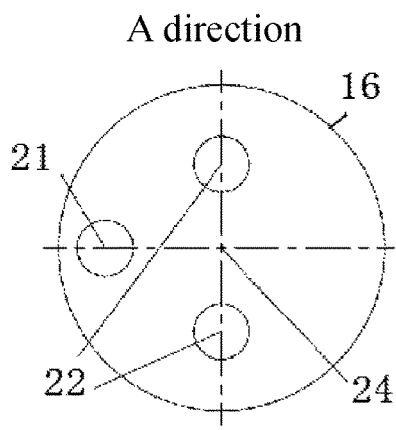
Figure 1c

ZOOM OBJECTIVE LENS OF OPERATING MICROSCOPE

CROSS REFERENCE TO RELATED APPLICATIONS

This application is a § 371 National State Application of PCT/CN2014/095429 filed Dec. 29, 2014 which claims priority to CN201410171856.5 filed Apr. 25, 2014, which are hereby incorporated by reference in their entirety.

FIELD OF INVENTION

The present invention relates to the field of medical optical instruments of medical instrumentation, in particular to a zoom objective lens of an operating microscope.

BACKGROUND OF THE INVENTION

The focal length of a wide-aperture objective lens of the usual operating microscopes is constant, and corresponding working distance and magnification times are certain. As shown in FIG. 1a, when it needs to change the focal length of the wide-aperture lens, it is achieved by switching to a lens Wa or Wb with different focal lengths, and the drawbacks are discontinuous change on the focal length of the objective lens, inconvenient replacement, affecting the use. There is a continuous zoom operating microscope system using a compensating lens moving non-linearly and a lens group moving linearly, which has a complex structure and a complicated process, and belongs to a different type.

SUMMARY OF THE INVENTION

The present invention is intended to provide a zoom objective lens of an operating microscope.

To achieve the above purpose, the technical schemes employed by the present invention are:

A zoom objective lens of an operating microscope, is provided along a same axis with the operating microscope, and comprises a positive lens group and a negative lens group provided along a same optical axis; the positive lens group is provided on an objective lens holder, and the negative lens group is provided on a negative lens group holder and directly faces the object under observation; the zoom objective lens is connected to a body of the operating microscope through the objective lens holder, the negative lens group holder is capable of moving in the optical axis direction relative to the objective lens holder, and the position of the positive lens group relative to an illumination group and an observation group remains unchanged.

Preferably, the zoom objective lens is changeably connected to the body of the operating microscope.

Preferably, the zoom objective lens further comprises a guide mechanism for leading the negative lens group holder to move in the optical axis direction, the guide mechanism comprising a guiding column fixed on the objective lens holder and a guiding slot provided on the negative lens group holder, the guiding column and the guiding slot being slidingly fitted.

Preferably, the zoom objective lens further comprises a guide mechanism for leading the negative lens group holder to move in the optical axis direction, the guide mechanism comprising a cylindrical fitted guiding surface provided on an inner cylinder wall of the objective lens holder, an outer cylinder wall of the negative lens group holder and the cylindrical fitted guiding surface being slidingly fitted.

More preferably, linear guiding slots are provided on two sides of the objective lens holder parallel to the optical axis, guiding pins are provided on the negative lens group holder, and the guiding pin is provided within the linear guiding slots slidably.

More preferably, the zoom objective lens further comprises a drive mechanism for driving the negative lens group holder to move in the optical axis direction, and the drive mechanism is a threaded swivel mechanism comprising a limit ring provided on a lower part of the objective lens holder and a threaded swivel provided coaxially to the optical axis and capable of rotating around the optical axis, the threaded swivel being sheathed on the objective lens holder above the limit ring, and being slidingly fitted with the guiding pin.

Preferably, the zoom objective lens further comprises a drive mechanism for driving the negative lens group holder to move in the optical axis direction, the drive mechanism comprising a rack provided on the negative lens group holder, a gear provided on the objective lens holder and matching up with the rack, and a drive shaft driving the gear to rotate relative to the rack.

Preferably, the zoom objective lens further comprises a drive mechanism for driving the negative lens group holder to move in the optical axis direction, the drive mechanism comprising a push plate provided on the negative lens group holder, an eccentric cam provided on the objective lens holder and a spinning wheel connected with the eccentric cam, a peripheral surface of the eccentric cam being against a bottom surface of the push plate.

Preferably, the zoom objective lens further comprises a drive mechanism for driving the negative lens group holder to move in the optical axis direction, the drive mechanism is a rocker-slider mechanism comprising long slots provided on two sides of the objective lens holder parallel to the optical axis, sliding blocks provided on the negative lens group holder and capable of sliding inside of the long slot, a rocker, and a pin connected to the rocker, a hole being provided on the sliding block and being running fitted with the pin.

Preferably, the zoom objective lens and the body of the operating microscope are connected by thread or clasp.

Due to the use of the above technical schemes, the present invention has the following advantages and effects over the prior art:

The zoom objective lens of the present invention has a focus length capable of being continuously adjusted, and can be replaced as an entirety; the original structures of the illuminating system and the observation system remain unchanged, and during zooming, the position of the zoom objective lens relatives to the illuminating system and the observation system remains unchanged, and meanwhile, the zoom objective lens is provided with a guiding mechanism and a drive mechanism for moving the negative lens group and focusing externally, has a compact structure, and is convenient for adjusting.

BRIEF DESCRIPTION OF THE DRAWINGS

FIG. 1a is a schematic diagram of an optical system of a zoom objective lens of an operating microscope in the prior art;

FIG. 1b is a schematic diagram of an optical system of a zoom objective lens of an operating microscope in the present invention;

FIG. 1c is a schematic diagram of FIG. 1b viewed along A direction;

Wherein:
10—operating microscope;
11, 111, 211—positive lens group;
12, 112, 212—negative lens group;
14, 114, 414—objective lens holder;
15, 115, 215—negative lens group holder;
16—zoom objective lens;
17, 117, 217—guiding mechanism;
18, 118, 218, 318—drive mechanism;
20—operating microscope body; 21—illumination group; 22—observation group;
24, 124, 224—optical axis;
25—sliding block; 26—rocker; 27—rocker rotary knob; 28—rocker pin;
30, 130—cylindrical fitted guiding surface;
31—guiding pin; 32—threaded swivel; 33—limit ring;
41—fixing element; 42—guiding column; 43—fitted surface of guiding column; 44—centric axis of guiding column;
51—rack; 52—gear; 53—drive shaft; 54—rotary knob; 55—micro motor;
61—spinning wheel; 62—eccentric cam; 63—push plate.

DETAILED DESCRIPTION OF EXEMPLARY EMBODIMENTS

Figure 2:
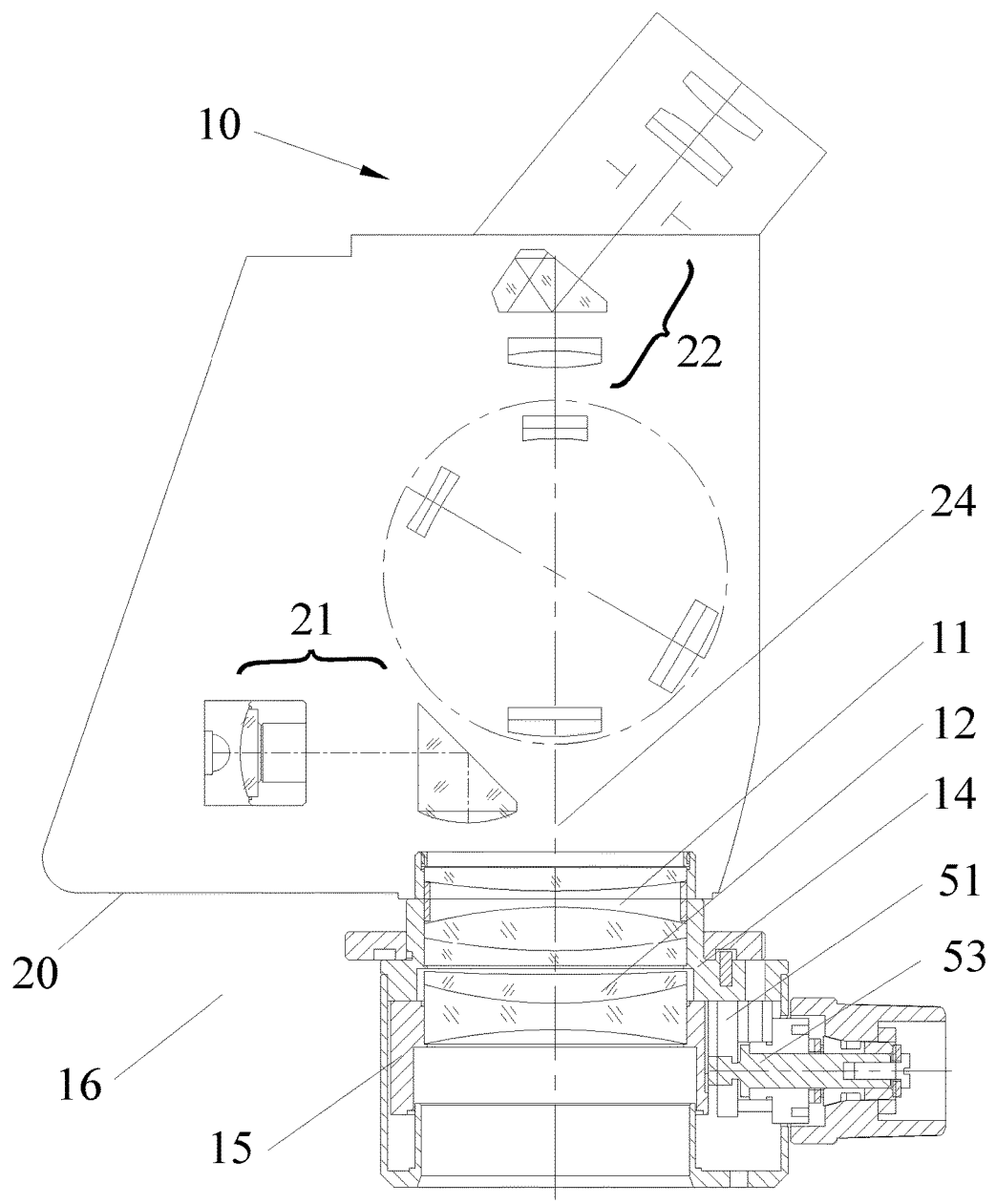
FIG. 2 is a overall structure schematic diagram of an optical system of a zoom objective lens of an operating microscope in the present invention.

In the following, the present invention are explained in detail combining the embodiments with the accompanying drawings:

As shown in Figures 1b, 1c and 2, a zoom objective lens 16 of an operating microscope, is provided along a same axis 24 with a lens cone of the operating microscope, and comprises a positive lens group 11 and a negative lens group 12 provided in the same optical axis 24 direction; the positive lens group 11 is provided on an objective lens holder 14, and the negative lens group 12 is provided on a negative lens group holder 15 and directly faces the object G under observation; the zoom objective lens 16 is connected to a body 20 of the operating microscope through the objective lens holder 15, the negative lens group holder 15 is capable of moving in the optical axis 24 direction relative to the objective lens holder 14, and the position of the objective lens holder 14 relative to an illumination group 21 and an observation group 22 remains unchanged.

The negative lens group holder 15 drives the negative lens group 12 to move in the optical axis 24 direction, causing that the focus length of the zoom objective lens 16 changes. When the space between the negative lens group 12 and the positive lens group 11 is decreased, the focus length of the zoom objective lens 16 is increased, and accordingly the working distance of observation of the operating microscope is also increased; and when the space between the negative lens group 12 and the positive lens group 11 is increased, the focus length of the zoom objective lens 16 is decreased correspondingly, and accordingly the working distance of observation of the operating microscope is also decreased.

The zoom objective lens 16 of the present invention is changeably connected to the body 20 of the operating microscope.

The zoom objective lens 16 and the body 20 of the operating microscope are connected by thread or clasp. The zoom objective lens 16 and the body 20 of the operating microscope can be replaced, and may be replaced by other zoom or fixed-focus objective lens, or may be rotate around the optical axis 24 according to requirements of use.

The design and calculation of the optical path of the zoom objective lens in this embodiment are as follow:

Setting the focus length of the positive lens group 11 to be 82.63 mm,

No—serial number of a positive lens; R—radius of curvature of the positive lens; D—distance between lenses; Nd—refraction index;

No.1 R:107.100 D:.000 Nd:1
No.2 R:−295.100 D:.3.600 Nd:1.5163
No.3 R:75.0000 D:.5.000 Nd:1
No.4 R:−186.680 D:.100 Nd:1.5163
No.5 R:.100000E+15 D:8.000 Nd:1.7172

Setting the focus length of the negative lens group 12 to be <89.46 mm,

No.1 R:−128.950 D:.000 Nd:1
No.2 R:128.950 D:.3.000 Nd:1.7172

Assuming that the positive lens group 11 does not move, the negative lens group 12 is moved to change the distance D between it and the positive lens group 11, and the focus length F of the whole objective lens continuously varies in linear manner.

The corresponding focus length F of the objective lens at varying distances: (mm)

Distance D: 25; 22; 18; 16; 15; 3.6
Focus length F: 202.4; 220.88; 251.5; 270.2; 280.7; 502.16.

As can be seen, when the distance D between the negative lens group 12 and the positive lens group 11 decreases, the focus length F of the whole objective lens increases.

Figure 3A:
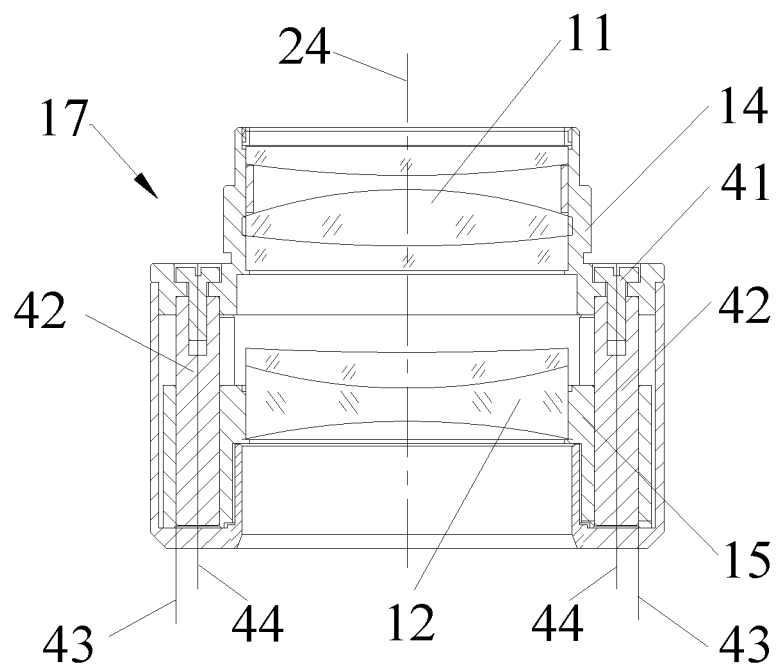
FIG. 3a is a structure schematic diagram of a guiding mechanism in the present invention (guiding by a guiding column)

The zoom objective lens 16 further comprises a guide mechanism for leading the negative lens group holder 15 to move in the optical axis 24 direction, and the following are some kinds of embodiments:

As shown in FIG. 3a, the guide mechanism 17 comprises a guiding column 42 fixed on the objective lens holder 14 via a fixing element 41, and a guiding slot provided on the negative lens group holder. The central axis of the guiding slot and the central axis 44 of the guiding column 42 coincide, the guiding slot is slidingly fitted with the cylindrical fitted guiding surface of the guiding column 42, and the central axis 44 of the guiding column 42 is parallel to the optical axis 24 of the negative lens group 12. In the present embodiment, a pair of guiding columns 42 is employed to cause the negative lens group holder 15 to move in the central axis 44 direction of the guiding column 42 parallel to the optical axis, to be uniformly forced and to work stably.

Figure 3B:
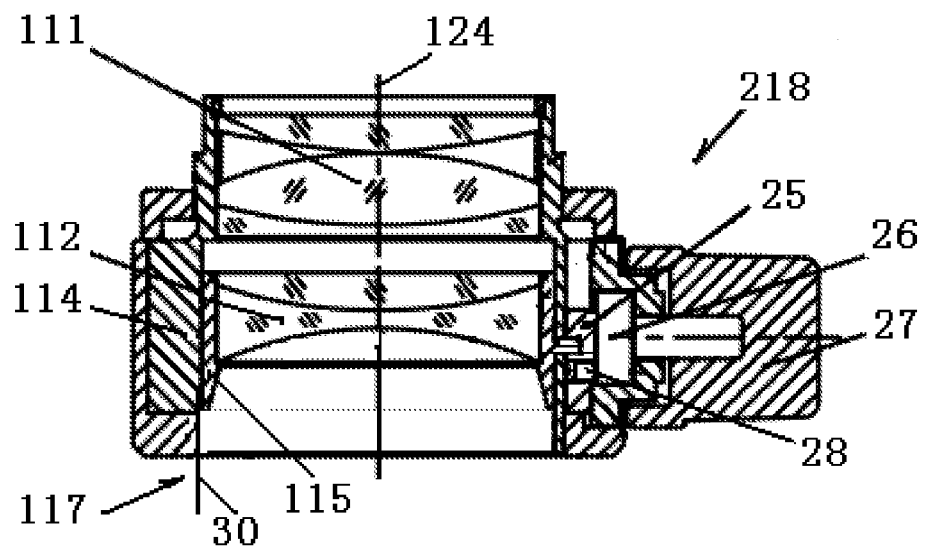
FIG. 3b is a structure schematic diagram of a guiding mechanism in the present invention (guiding by a cylindrical fitted guiding surface)

As shown in FIG. 3b, the guide mechanism 117 comprises a cylindrical fitted guiding surface 30 provided on an inner cylinder wall of the objective lens holder 114, and an outer cylinder wall of the negative lens group holder 115 and the cylindrical fitted guiding surface 30 are slidingly fitted.

Figure 7:
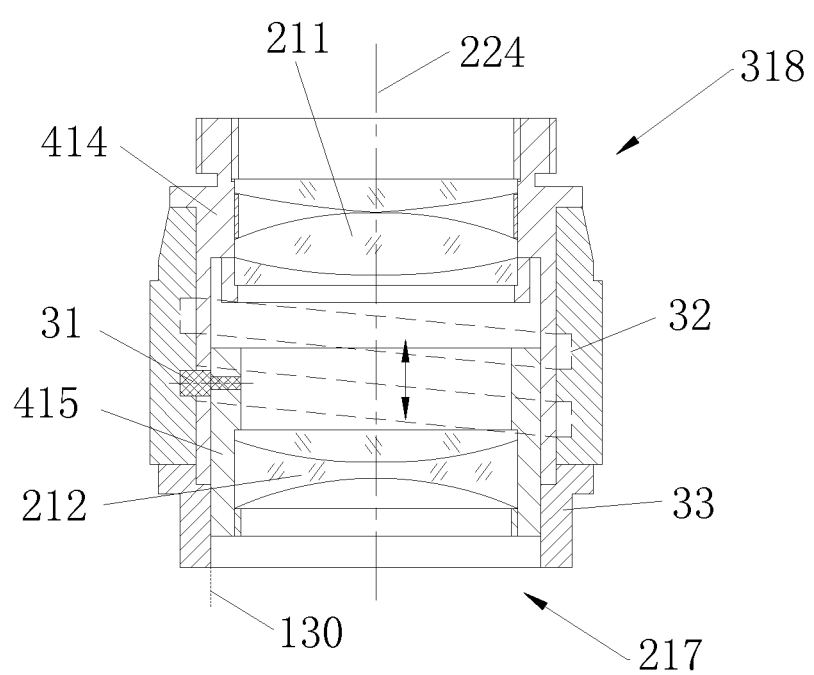
FIG. 7 is a structure schematic diagram of a guiding mechanism and a drive mechanism in the present invention (guiding by a cylindrical fitted guiding surface, and threaded swivel transmission).

As shown in FIG. 7, the guide mechanism 217 comprises a cylindrical fitted guiding surface 130 provided on an inner cylinder wall of the objective lens holder 414, and an outer cylinder wall of the and the cylindrical fitted guiding surface 130 are slidingly fitted, and meanwhile, linear guiding slots are provided on two sides of the objective lens holder 414 parallel to the optical axis 224, guiding pins 31 are provided on the negative lens group holder 415, the guiding pin 31 is provided within the linear guiding slot slidably, and the negative lens group holder 415 is driven to move along the axial direction by sliding the guiding pin 31 in the guiding slot.

Figure 4A:
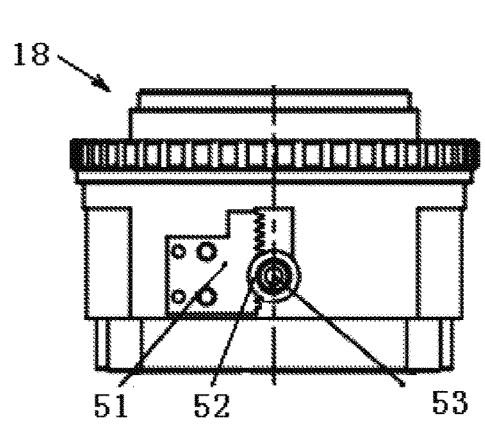
FIGS. 4a and 4b are structure schematic diagrams of a drive mechanism in the present invention (gear-rack transmission)
Figure 4B:
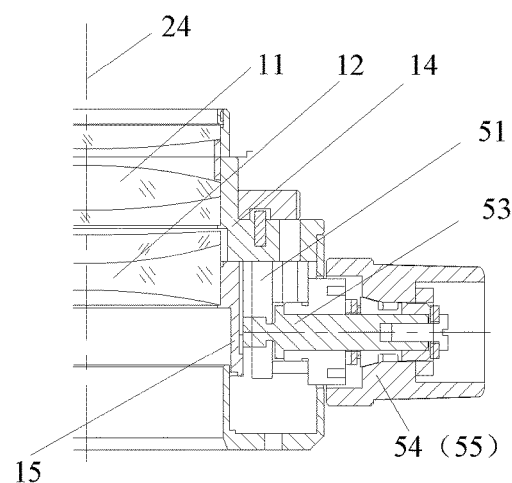

The zoom objective lens 16 further comprises a driving mechanism for driving the negative lens group holder 15 to move in the optical axis 24 direction, and the following are some kinds of embodiments:

As shown in FIGS. 4a and 4b, the drive mechanism 18 comprises a rack 51 provided on the negative lens group holder 15, a gear 52 provided on the objective lens holder 14 and matching up with the rack 51, and a drive shaft 53 driving the gear 52 to rotate relative to the rack 51, and the drive mechanism 18 is driven to operate by rotating the drive shaft 53

Figure 5:
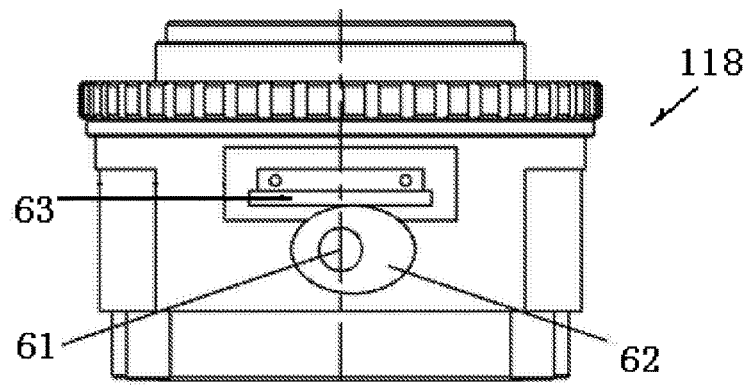
FIG. 5 is a structure schematic diagram of a drive mechanism in the present invention (cam-push plate transmission)

As shown in FIG. 5, the drive mechanism 118 is a cam-push plate mechanism, and comprises a push plate 63 provided on the negative lens group holder 15, an eccentric cam 62 provided on the objective lens holder 14 and a spinning wheel 61 connected with the eccentric cam 62, a peripheral surface of the eccentric cam 61 being against a bottom surface of the push plate 63, and the drive mechanism 118 is driven to operate by sliding the eccentric cam 63 on the bottom surface of the push plate 63.

Figure 6:
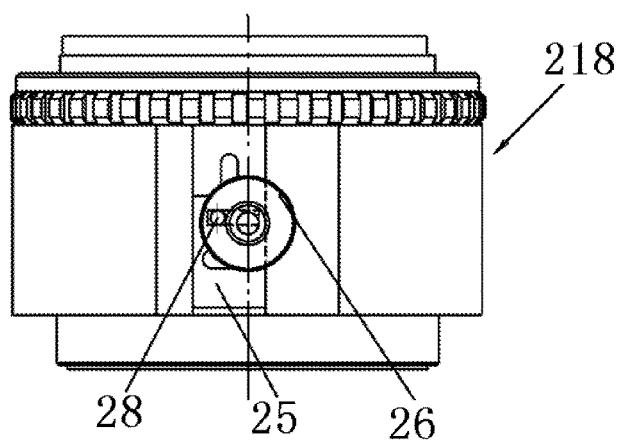
FIG. 6 is a structure schematic diagram of a drive mechanism in the present invention (rocker-slider transmission)

As shown in FIGS. 6 and 3b, the drive mechanism 218 is a rocker-slider mechanism, and comprises long slots provided on two sides of the objective lens holder 114 parallel to the optical axis 124, a sliding block 25 provided on the negative lens group holder 115 and capable of sliding inside the straight slots of the objective lens holder 114, a rocker 26, and a pin 28 connected to the rocker 26, a hole being provided on the sliding block 25 and being running fitted with the pin 28, and the sliding block 25 and the negative lens group holder 115 are driven to move by the pin 28 on the rocker 26.

As shown in FIG. 7, the drive mechanism 318 is a threaded swivel mechanism, cooperates with the guiding mechanism 217, and comprises a limit ring 33 provided on a lower part of the objective lens holder 414 and a threaded swivel 32 provided coaxially to the optical axis 224 and capable of rotating around the optical axis 224, the threaded swivel 32 being sheathed on the objective lens holder 414 above the limit ring 33, and being slidingly fitted with the guiding pin 31, the negative lens group holder 415 is driven to operate by rotating the threaded swivel 32 and driving the guiding pin 31 to slide in the guiding slot.

The drive shaft 53 in the above-mentioned drive mechanism may employ a rotary knob 54 or a micro-motor 55 instead to operate.

The embodiments described above are only for illustrating the technical concepts and features of the present invention, and intended to make those skilled in the art being able to understand the present invention and thereby implement it, and should not be concluded to limit the protective scope of this invention. Any equivalent variations or modifications according to the present invention should be covered by the protective scope of the present invention.

What is claimed is:

1. A zoom objective lens of an operating microscope, being provided along a same axis with a lens core of the operating microscope, and comprising a positive lens group and a negative lens group provided along a same optical axis, wherein,
    the positive lens group is provided on an objective lens holder, and the negative lens group is provided on a negative lens group holder and directly faces the object under observation; the zoom objective lens is connected to a body of the operating microscope through the objective lens holder, the negative lens group holder is capable of moving in the optical axis direction relative to the objective lens holder, and the position of the positive lens group relative to an illumination group and an observation group remains unchanged.

2. The zoom objective lens of an operating microscope according to claim 1, wherein,
    the zoom objective lens is changeably connected to the body of the operating microscope.

3. The zoom objective lens of an operating microscope according to claim 2, wherein,
    the zoom objective lens further comprises a guide mechanism for leading the negative lens group holder to move in the optical axis direction, the guide mechanism comprising a guiding column fixed on the objective lens holder and a guiding slot provided on the negative lens group holder, the guiding column and the guiding slot being slidingly fitted.

4. The zoom objective lens of an operating microscope according to claim 2, wherein,
    the zoom objective lens further comprises a guide mechanism for leading the negative lens group holder to move in the optical axis direction, the guide mechanism comprising a cylindrical fitted guiding surface provided on an inner cylinder wall of the objective lens holder, an outer cylinder wall of the negative lens group holder and the cylindrical fitted guiding surface being slidingly fitted.

5. The zoom objective lens of an operating microscope according to claim 4, wherein,
    linear guiding slots are provided on two sides of the objective lens holder parallel to the optical axis, guiding pins are provided on the negative lens group holder, and the guiding pin is provided within the linear guiding slots slidably.

6. The zoom objective lens of an operating microscope according to claim 5, wherein,
    the zoom objective lens further comprises a drive mechanism for driving the negative lens group holder to move in the optical axis direction, and the drive mechanism comprising a limit ring provided on a lower part of the objective lens holder and a threaded swivel provided coaxially to the optical axis and capable of rotating around the optical axis, the threaded swivel being sheathed on the objective lens holder above the limit ring, and being slidingly fitted with the guiding pins.

7. The zoom objective lens of an operating microscope according to claim 2, wherein,
    the zoom objective lens further comprises a drive mechanism for driving the negative lens group holder to move in the optical axis direction, the drive mechanism comprising a rack provided on the negative lens group holder, a gear provided on the objective lens holder and matching up with the rack, and a drive shaft driving the gear to rotate relative to the rack.

8. The zoom objective lens of an operating microscope according to claim 2, wherein,
the zoom objective lens further comprises a drive mechanism for driving the negative lens group holder to move in the optical axis direction, the drive mechanism comprising a push plate provided on the negative lens group holder, an eccentric cam provided on the objective lens holder and a spinning wheel connected with the eccentric cam, a peripheral surface of the eccentric cam being against a bottom surface of the push plate.

9. The zoom objective lens of an operating microscope according to claim 2, wherein,
the zoom objective lens further comprises a drive mechanism for driving the negative lens group holder to move in the optical axis direction, the drive mechanism is a rocker-slider mechanism comprising long slots provided on two sides of the objective lens holder parallel to the optical axis, sliding blocks provided on the negative lens group holder and capable of sliding inside of the long slot, a rocker, and a pin connected to the rocker, a hole being provided on the sliding block and being running fitted with the pin.

10. The zoom objective lens of an operating microscope according to claim 2, wherein,
the zoom objective lens and the body of the operating microscope are connected by thread or clasp.

11. The zoom objective lens of an operating microscope according to claim 1, wherein,
the zoom objective lens further comprises a guide mechanism for leading the negative lens group holder to move in the optical axis direction, the guide mechanism comprising a guiding column fixed on the objective lens holder and a guiding slot provided on the negative lens group holder, the guiding column and the guiding slot being slidingly fitted.

12. The zoom objective lens of an operating microscope according to claim 1, wherein,
the zoom objective lens further comprises a guide mechanism for leading the negative lens group holder to move in the optical axis direction, the guide mechanism comprising a cylindrical fitted guiding surface provided on an inner cylinder wall of the objective lens holder, an outer cylinder wall of the negative lens group holder and the cylindrical fitted guiding surface being slidingly fitted.

13. The zoom objective lens of an operating microscope according to claim 12, wherein,
linear guiding slots are provided on two sides of the objective lens holder parallel to the optical axis, guiding pins are provided on the negative lens group holder, and the guiding pin is provided within the linear guiding slots slidably.

14. The zoom objective lens of an operating microscope according to claim 13, wherein,
the zoom objective lens further comprises a drive mechanism for driving the negative lens group holder to move in the optical axis direction, and the drive mechanism comprising a limit ring provided on a lower part of the objective lens holder and a threaded swivel provided coaxially to the optical axis and capable of rotating around the optical axis, the threaded swivel being sheathed on the objective lens holder above the limit ring, and being slidingly fitted with the guiding pins.

15. The zoom objective lens of an operating microscope according to claim 1, wherein,
the zoom objective lens further comprises a drive mechanism for driving the negative lens group holder to move in the optical axis direction, the drive mechanism comprising a rack provided on the negative lens group holder, a gear provided on the objective lens holder and matching up with the rack, and a drive shaft driving the gear to rotate relative to the rack.

16. The zoom objective lens of an operating microscope according to claim 1, wherein,
the zoom objective lens further comprises a drive mechanism for driving the negative lens group holder to move in the optical axis direction, the drive mechanism comprising a push plate provided on the negative lens group holder, an eccentric cam provided on the objective lens holder and a spinning wheel connected with the eccentric cam, a peripheral surface of the eccentric cam being against a bottom surface of the push plate.

17. The zoom objective lens of an operating microscope according to claim 1, wherein,
the zoom objective lens further comprises a drive mechanism for driving the negative lens group holder to move in the optical axis direction, the drive mechanism is a rocker-slider mechanism comprising long slots provided on two sides of the objective lens holder parallel to the optical axis, sliding blocks provided on the negative lens group holder and capable of sliding inside of the long slot, a rocker, and a pin connected to the rocker, a hole being provided on the sliding block and being running fitted with the pin.

18. The zoom objective lens of an operating microscope according to claim 1, wherein,
the zoom objective lens and the body of the operating microscope are connected by thread or clasp.

* * * * *